US00PP17653P2

(12) United States Plant Patent
Crowther

(10) Patent No.: US PP17,653 P2
(45) Date of Patent: Apr. 24, 2007

(54) ***YUCCA* PLANT NAMED 'WALBRISTAR'**

(50) Latin Name: ***Yucca gloriosa* var. *recurvifolia***
Varietal Denomination: WALBRISTAR

(76) Inventor: Albert Timothy Crowther, Walberton Nursery, Yapton Lane, Arundel (GB), BN18 OAS ( * ) Notice: Subject to any disclaimer, the term of this patent is extended or adjusted under 35 U.S.C. 154(b) by 20 days.

(21) Appl. No.: 11/293,741

(22) Filed: Dec. 1, 2005

(51) Int. Cl.
*A01H 5/00* (2006.01)

(52) U.S. Cl. ..... Plt./373
(58) Field of Classification Search ..... Plt./373
See application file for complete search history.

*Primary Examiner*—Kent Bell
*Assistant Examiner*—Annette H Para

(57) ABSTRACT

A new cultivar of *Yucca* plant named 'WALBRISTAR' whose leaves are characterized by broader and deeper yellow margins than all other existing varieties of *Yucca* known to the inventor.

1 Drawing Sheet

Genus: *Yucca.*
Species: *gloriosa* var. *recurvifolia.*
Denomination: WALBRISTAR.

BACKGROUND OF THE INVENTION

The present invention relates to a new and distinct variety of Spanish dagger grown for use as an ornamental for container or the landscape. The new cultivar is known botanically as *Yucca gloriosa* var. *recurvifolia* and will be referred to hereinafter by the cultivar name 'WALBRISTAR'.

The species of *Yucca* known as *Yucca gloriosa* is native to the sand dunes of the south eastern United States. *Yucca gloriosa* carries rigid upright leaves with a smooth underside. During the 1920s, many hybrids of *Yucca gloriosa* were introduced to cultivation, either as hybrids within the species, or as hybrids with other species of *Yucca* including *Yucca aloifolia, Yucca filamentosa* or *Yucca flaccida.* Of these hybrids, some selections have continued to be classified as *Yucca gloriosa* whilst others which exhibit flexible and recurving foliage have been classified as *Yucca recurvifolia.* In addition, the leaves of plants described as *Yucca recurvifolia* are generally observed to have a rough underside. Because 'WALBRISTAR' originated in a crop of plants which have been known and described as variegated *Yucca gloriosa,* but because the leaves of 'WALBRISTAR' tend to recurve and have a rough underside, then the inventor considers that the most representative designation of the species is *Yucca gloriosa* var. *recurvifolia.* However, it appears to be industry practice to condense this designation to *Yucca recurvifolia.*

Each year, the inventor propagates *Yucca* by removing the side shoots, commonly known as "pups", from the base of the stems of the parent plants of variegated *Yucca gloriosa* (unpatented). In 2000, in the course of this propagation, the inventor observed one side shoot whose rosette of foliage was atypical of the parent. Approximately one half side of this atypical rosette exhibited a greater degree of golden variegation. The inventor removed this one side shoot with the intention of attempting to produce a new plant form whose entire rosette would exhibit a uniformly more golden variegation. The inventor rooted the first-discovered side shoot and removed its growing point in order to encourage rapid basal side shoot production. In 2001, the inventor observed that three side shoots had arisen with varying degrees of golden variegation. The inventor observed that one of these three side shoots exhibited a uniform and significant degree of golden variegation. This one side shoot, 'WALBRISTAR', was removed and transferred to the inventor's tissue culture laboratory where it was successfully initiated into culture and then multiplied by the same method of removing basal shoot cuttings, but in vitro.

'WALBRISTAR' was first asexually propagated from basal shoot cuttings in vitro which were deflasked during 2002 and rooted in ordinary peat-based growing medium. The inventor observed the resulting crop of plants and determined that the original characteristics of 'WALBRISTAR' had been reproduced identically, and that 'WALBRISTAR' is stable and reproduces true to type.

When compared with other varieties of *Yucca gloriosa* or *Yucca recurvifolia* known to the inventor, and also in comparison with its parent, 'WALBRISTAR' exhibits a much broader and deeper colored yellow margin. 'WALBRISTAR' also exhibits a more lax habit than its parent and is also slower growing than its parent.

'WALBRISTAR' has produced no flowers to date.

SUMMARY OF THE INVENTION

The following traits have been repeatedly observed and represent the distinguishing characteristics of the new *Yucca* variety named 'WALBRISTAR'. In combination these traits set 'WALBRISTAR' apart from all other varieties of *Yucca* known to the inventor. 'WALBRISTAR' has not been tested under all possible conditions and phenotypic differences may be observed with variations in environmental, climatic and cultural conditions, however, without any variance in genotype.

1. 'WALBRISTAR' exhibits upright and recurving leaves.
2. The leaves of 'WALBRISTAR' exhibit broad, deep yellow margins.
3. The undersides of the leaves of 'WALBRISTAR' are slightly rough.
4. 'WALBRISTAR' is slow growing.

BRIEF DESCRIPTION OF THE DRAWING

The accompanying color drawing

Figure 1:
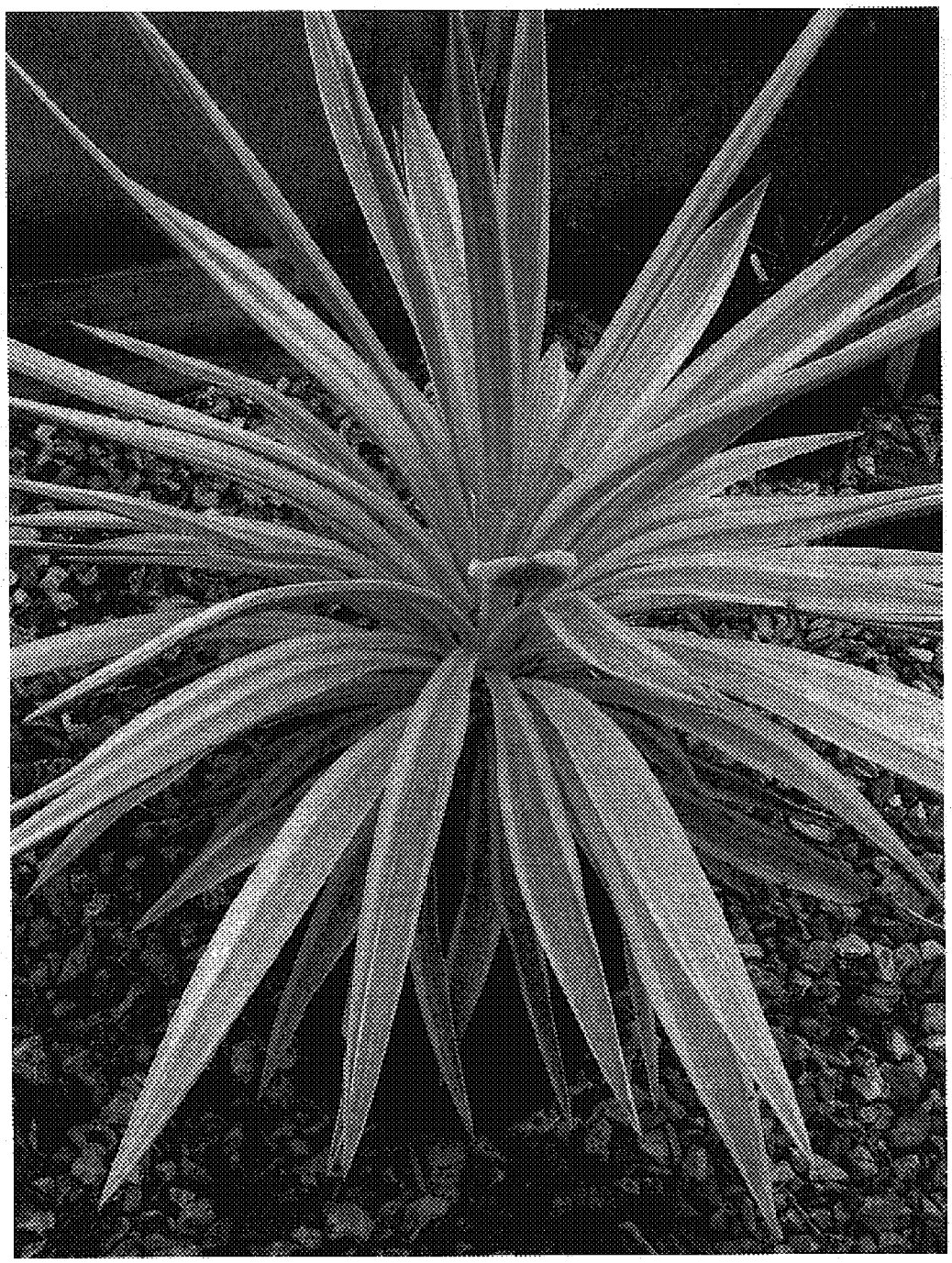
FIG. 1 illustrates the overall appearance of 'WALBRISTAR' showing the colors as true as it is reasonably possible to obtain in colored reproductions of this type. Colors in the drawing may differ from the color values cited in the detailed botanical description, which accurately describe the actual colors of the new variety 'WALBRISTAR'.

The plant in FIG. 1 is approximately 2 years old and has been grown out-of-doors in a 2 gallon container in Arroyo Grande, Calif.

BOTANICAL DESCRIPTION OF THE PLANT

The following is a detailed description of the new *Yucca gloriosa* var. *recurvifolia* plant named 'WALBRISTAR'. Data was collected in Arroyo Grande, Calif. from a 27-month-old plant growing out-of-doors in a 5-liter commercial container. The color determinations are in accordance with the 2001 edition of The Royal Horticultural Society Colour Chart, London, England, except where general color terms of ordinary dictionary significance are used. The growing requirements are similar to other *Yucca*.

Botanical classification: *Yucca gloriosa* var. *recurvifolia* 'WALBRISTAR'.
Genus: *Yucca*.
Species: *gloriosa* var *recurvifolia*.
Denomination: 'WALBRISTAR'.
Common name: Spanish dagger.
Commercial classification: Ornamental shrub.
Plant use: Container or landscape plant.
Cultural requirements: Cultural requirements are well draining loam soil, full sun and minimal water.
Root system: Fine and fibrous.
Plant vigor: Moderate vigor.
Plant growth rate: Slow growing.
Parentage: Spontaneous basal branch sport from an unnamed selection of variegated *Yucca gloriosa* (unpatented).
Plant description:
- *Bloom period.*—'WALBRISTAR' has produced no flowers to date.
- *Plant habit.*—Tight rosette habit when young. Older foliage tends to recurve.
- *Plant height.*—Plant is 50 cm. in height in a 5-liter commercial container.
- *Plant width.*—Plant is 94 cm. in width in a 5-liter commercial container.
- *Plant hardiness.*—Plant is hardy to USDA Zone 7.
- *Propagation.*—Propagation is accomplished by taking shoot cuttings in tissue culture.
- *Time to develop roots.*—2 months is needed to develop roots by the method of tissue culture.
- *Crop time.*—From 9 to 12 months is needed to produce a 1-liter commercial container plant.
- *Disease susceptibility and resistance.*—Like other Yuccas under nursery conditions 'WALBRISTAR' can suffer from leaf spot diseases for example *Cercospora concentrica* or *Coniothyrium concentricum.* No further disease susceptibility of 'WALBRISTAR' is known to the inventor.
- *Special growing considerations.*—Requires careful placement away from walkways and foot traffic; and will tolerate poor sandy soil.

Stem:
- *Stem type.*—Caudex.
- *Stem shape.*—Cylindrical in shape.
- *Stem color.*—Individual colors 191A and 11B are present on an individual stem.
- *Stem diameter on a plant in a 5 liter container.*—9 cm in diameter.
- *Stem height.*—14 cm in height.
- *Stem surface.*—Bases of imbricate leaves comprise the caudex stem surface.

Foliage:
- *Foliage type.*—Evergreen.
- *Quantity of leaves.*—Leaves on a 5-liter commercial container plant range from 80 to 100 in number.
- *Leaf shape.*—Lanceolate in shape, with slightly involute edges that become pronounced at the apex.
- *Leaf division.*—Simple.
- *Leaf arrangement.*—Spirally arranged.
- *Leaf apex.*—Sharp apex.
- *Shape of apical spine.*—Triangular in shape.
- *Color of apical spine.*—182A.
- *Length of apical spine.*—6 mm. in length.
- *Leaf base.*—Truncate base.
- *Venation pattern.*—Inconspicuous parallel vein pattern.
- *Vein color* (*adaxial and abaxial surfaces*).—Veins are inconspicuous and closest to 191B in color.
- *Leaf margins.*—Entire.
- *Leaf attachment.*—Sheathing.
- *Leaf surface* (*adaxial*).—Smooth.
- *Leaf surface* (*abaxial*).—Muriculate.
- *Leaf pubescence.*—None observed.
- *Leaf width.*—4.75 cm.
- *Leaf length.*—48 cm.
- *Leaf color.*—Juvenile or upright leaves (adaxial and abaxial surfaces): 139B and 139C with broad edges 13A each extending along the entire leaf length and extending inwards from the margin to approximately one fifth of the leaf width. Mature recurving leaves (adaxial and abaxial surfaces): 193B with broad edges 11C each extending along the entire leaf length and extending inwards from the margin to approximately one fifth of the leaf width.
- *Leaf fragrance.*—No fragrance observed.

Flowers: No flowers have been produced to date.

It is claimed:

1. A new and distinct cultivar of *Yucca* plant named 'WALBRISTAR' as described and illustrated herein.

* * * * *